(12) United States Patent
Martello (10) Patent No.: US 6,551,234 B1
(45) Date of Patent: *Apr. 22, 2003

(54) THERAPEUTIC MAGNET BELT

(76) Inventor: Matthew Philip Martello, P.O. Box 581, Concord, CA (US) 94522-0581

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/844,791

(22) Filed: Apr. 26, 2001

Related U.S. Application Data (60) Provisional application No. 60/199,793, filed on Apr. 26, 2000.

(51) Int. Cl.[7] ............................................. A61N 1/00
(52) U.S. Cl. ...................................................... 600/15
(58) Field of Search ........................................ 600/9–15

(56) References Cited

U.S. PATENT DOCUMENTS

| | | | |
|---|---|---|---|
| 3,921,620 A | * 11/1975 | Nakayama | 600/15 |
| 3,943,912 A | * 3/1976 | Nakayama | 600/15 |
| 5,707,333 A | * 1/1998 | Bakst | 600/15 |
| 5,738,624 A | * 4/1998 | Zablotsky et al. | 600/15 |

* cited by examiner

*Primary Examiner*—John P. Lacyk (57) ABSTRACT

A vertically-oversized belt supporting specially-strong magnets whose strategic exposure over a selected area of a wearer's torso, including the belly, buttocks, back, lateral or upper abdomen, progressively disintegrates fat and discourages its storage there. More specifically, a plurality of magnets are arranged on the larger center of a supporting portion whose flexibility and overlapping left strap and right strap, with their interlocking left slit and right slit, form a flap-in-slot fastener that attaches the whole belt around the wearer's torso. To reinforce this snug-fitting attachment, an accessory magnet can optionally be placed magnetically over the interlocking, overlapping straps. The prolonged wearability of this magnetic apparatus enables enough exposure to magnetic fields of sufficient strength and surface area to reduce musculoskeletal pain and counteract fat within the wearer's torso, thereby improving health and appearance.

31 Claims, 8 Drawing Sheets

THERAPEUTIC MAGNET BELT

CROSS-REFERENCE TO RELATED APPLICATIONS

This application claims the benefit of Provisional Patent Application Ser. No. 60/199,793 filed on Apr. 26, 2000.

BACKGROUND

This invention relates to magnet therapy, specifically to a strategic magnetic applicator that discourages fat deposition and decreases fat stored within the human torso, which thus lowers total body fat too. Further therapeutic effects, including pain relief, can be achieved with this magnetic invention.

Growing in prevalence even globally, obesity is estimated by the World Health Organization as affecting 1.2 billion people. The Centers for Disease Control, Federal Trade Commission, and Food and Drug Administration (FDA) estimate the annual American "weight-loss" and obesity-related costs at $100 billion. Unfortunately, obesity is a causal factor in many disorders, including heart disease, diabetes, cancer, and musculoskeletal problems such as lower back pain.

Evidently, none of the following "weight loss" options are working: low-fat foods and beverages; best-selling "fad diet" books; commercial "weight loss" centers; health clubs; home exercise equipment; over-the-counter "fat-burning" supplements; and prescription diet drugs. According to the FDA Consumer Studies on Weight Loss Practices across America, "Attempted weight loss is a common behavior, regardless of age, gender, or ethnicity, and weight loss goals are substantial; however, obesity remains a major public health problem in the United States."

A number of commercially-available magnetic devices are designed only for lower back pain relief, many of which are not even effective for this purpose. None of these magnetic devices can decrease fat.

Hence, a need exists for a fat-loss method and apparatus whose effectiveness also embraces safety and practicality in reversing obesity as well as addresses its related disorders, such as back pain.

SUMMARY

A therapeutic magnet belt for decreasing fat content of a selected portion of a human body and for decreasing musculoskeletal pain is disclosed. In one embodiment of the invention, the therapeutic magnet belt includes a supporting portion and a plurality of magnets attached thereto, each of said plurality of magnets having a magnetic field strength from about 4,000 to about 40,000 gauss.

These and other features, aspects, and advantages of the therapeutic magnetic belt in its various embodiments will become apparent after consideration of the ensuing description, the accompanying drawings, and the appended claims.

DRAWING FIGURES

Like components are designated by like reference numerals in all figures, which are not necessarily drawn to scale.

REFERENCE NUMERALS IN DRAWINGS
Number and Part Name:
110 magnet
112 magnet array
114 supporting portion
116 larger center
118 left strap
120 right strap
122 left slit
124 right slit
126 flap-in-slot fastener
128 accessory magnet
130 rounded edge
132 extra slit
134 alternative magnet
136 alternative magnet array
138 reticulated weave supporting portion
140 non-circuitous supporting portion
142 non-magnetizable material
144 non-magnetizable supporting portion
146 additional attachment means
148 additional magnetic attachment means
150 perforated supporting portion
152 single-strap supporting portion
154 sheath
156 hook-and-loop fastener
158 large hook-in-a-loop fastener
160 hook-in-loop-clasp fastener
162 buckle fastener
164 button fastener
166 snap fastener
168 clip fastener
170 clamp fastener
172 plurality of ties fastener
174 flexible magnetic strip
176 adhesive magnetic apparatus
178 non-circuitous strap-less supporting portion
180 adhesive layer
182 non-contour supporting portion DETAILED DESCRIPTION—FIGS. 1 to 28

Throughout the following description, specific details are set forth in order to provide a more thorough understanding of the invention. However, the invention may be practiced without these particulars. In other instances, well-known elements have not been shown or described to avoid unnecessarily obscuring the invention. Accordingly, the specification and drawings are to be regarded in an illustrative, rather than a restrictive, sense.

Figure 1:
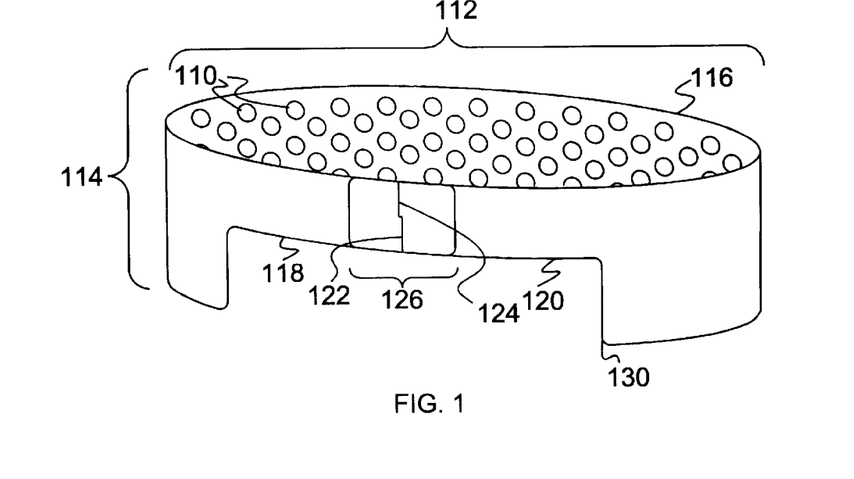
FIG. 1 shows a preferable embodiment of a therapeutic magnet belt, or "belt," through a view that reveals its inner surface supporting the magnets, plus its outer straps for fastening.

FIG. 1 shows one particular embodiment of the therapeutic magnet belt according to the invention. The belt includes a plurality of magnets 110, each having sufficient strength for fat-decreasing and pain-reducing effects. More specifically, their magnetic field strength ranges from about 4,000 to about 40,000 gauss. Furthermore, a magnet array 112 comprising plurality of magnets 110 strategically supplies sufficient magnetic field distribution, in terms of density and expansiveness, to affect a substantial area of the belt-wearer's torso. Magnet array 112 is attached to a supporting portion 114 that is rigid and flexible enough to act as a non-creasing stabilizer and contour-conformable applicator to achieve fat-decreasing and pain-reducing effects.

Supporting portion 114 comprises a larger center 116, a rounded edge 130, a left strap 118, a right strap 120, a left slit 122, and a right slit 124. Supporting portion 114 is magnetizable, so magnet array 112 adheres magnetically to the inner surface of the larger center 116 of the supporting portion. The narrower extensions of supporting portion 114 comprise the left strap 118 and right strap 120 that overlap when wrapped flexibly around the belt-wearer's whole torso. The left slit 122 and right slit 124 on left strap 118 and right strap 120, respectively, enable the overlapping straps to interlock through a flap-in-slot fastener 126. Thus, supporting portion 114 also includes the flap-in-slot fastener that is formed from the overlapping straps' slits that interlock in hook-and-eye fashion.

Thus, the belt is fastened around the wearer's torso so magnet array 112 on larger center 116 closely covers his or her targeted torso areas, which could include the belly, buttocks, back, lateral or upper abdomen. By simply wearing the belt, proper magnetic field exposure can be intimately sustained for sufficient time to decrease body fat, or reduce pain associated with musculoskeletal problems, or both.

Figure 2:
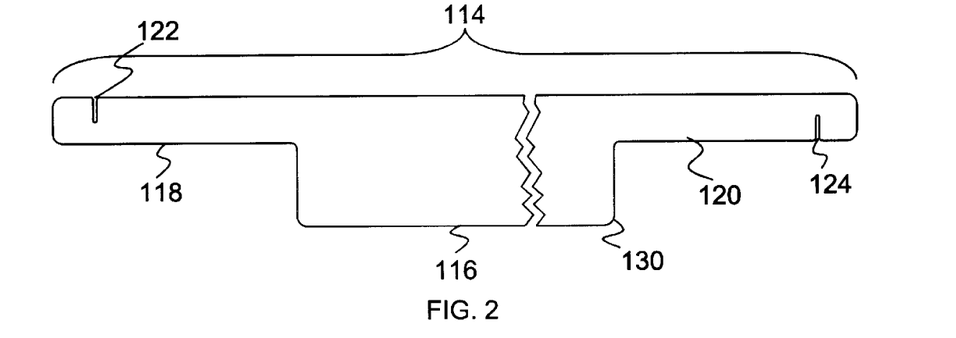
FIG. 2 shows only the supporting portion of the belt of FIG. 1, with its larger center and narrower straps with slits.

FIG. 2 shows only the supporting portion 114 of the belt of FIG. 1. Supporting portion 114 is preferably made of solid yet flexible steel, e.g., "galvanized flashing," because this material is practical in terms of availability and economy, and functional in that a solid supporting portion serves as a shield against magnetically-attracted objects outside the belt. Alternatively, the supporting portion could comprise a magnetizable metal other than steel, e.g., an alloy including cobalt, nickel, or iron.

Supporting portion 114 is preferably between about 0.01 and 0.03 inches in thickness, because magnetizable metal in this dimension range is thick enough to have durability and adequate attractive force with the magnets, and is thin enough to be concealable and flexible for wearability. However, the supporting portion could be thicker or thinner, and thus the given dimension range may be expanded.

A likely range for the overall breadth of supporting portion 114 is about 30 to 60 inches. However, the overall breadth of the belt's supporting portion will vary according to each wearer's torso circumference. For instance, a morbidly obese person would need a much wider belt than a slightly obese person.

Supporting portion 114 is shaped with a larger center that tapers into two narrower straps. Although the supporting portion could be shaped more or less closely to one's body contour, the basic T-formation of supporting portion 114 fits functionally, and makes assembly easy. Each of the T-shaped supporting portion's outer-pointing corners have a rounded edge 130 so the belt does not have sharp edges that scrape the skin.

Supporting portion 114 is shaped with the larger center 116 that offers enough surface area to cover fatty torso regions, such as the lower lateral and anterior abdomen, with the attached magnets. A likely range for the overall height of the larger center 116 of supporting portion 114 is about four to eight inches. Furthermore, a likely range for the breadth of larger center 116 is about 20 to 50 inches. However, the height and breadth of the belt's larger center will specifically vary according to the size of each wearer's targeted torso area.

Supporting portion 114 is further shaped with two narrower extensions, namely left strap 118 and right strap 120, that continue from the left and right ends of the larger center 116. Both straps are narrow enough to allow comfortable clearance of material around one's mobile torso. Yet, at the same time, both straps have enough height to offer sufficient vertical overlap of sturdy flaps for secure attachment. For example, straps that are about two inches high are functional for fastening, although other dimensions will also work.

The straps are also sufficiently broad to offer enough horizontal overlap of sturdy sections for secure attachment around the wearer's torso. For example, straps that have about a four-inch horizontal overlap are functional for fastening, although other dimensions will also work.

The specific dimensions of belt straps will differ according to each wearer's torso circumference. In general, left strap 118 and right strap 120 supply enough surface area to wrap and overlap around the wearer's torso so they join together through the "flap-in-slot" fastener 126, thereby attaching the belt.

More specifically, left strap 118 has the left slit 122 cut vertically into its top edge. Conversely, right strap 120 has the right slit 124 cut vertically into its bottom edge. Both slits are deep enough to establish secure slots, but not too deep to make the flaps flimsy. For example, one-inch slits are functional, although other depths are possible.

Furthermore, left slit 122 and right slit 124 occur at appropriately-spaced points so when the straps overlap around the wearer's torso, they can be insertionally interlaid to fittingly interlock. This connection is similar to a combination of dovetail joint and hook-and-eye fastener, but it is labeled as "flap-in-slot" fastener 126. Basically, both slits create receptive slots and rigid flaps that get hooked into each other when inserted by the belt-wearer's fingers or otherwise.

Left slit 122 and right slit 124 are positioned at a short distance horizontally in from their respective outermost edge of the belt. For example, each slit could be cut at a point about two inches horizontally in from each respective outermost edge. However, positioning of slits will vary between belts and even within the same belt. More specifically, in the likely event of the belt-wearer's torso shriking over time, new slits are easily cut at appropriate points for adjustability.

So, variations on the dimensions, orientations, or positions of the straps' slits may be arranged. For instance, one-and-a-half-inch and half-inch slits could be cut instead of two one-inch slits. Or, a slit may be cut from the bottom of the left strap and from the top of the right strap, instead of vice versa as previously specified.

Supporting portion 114 may be substituted by another supporting portion subsequently described in other belt embodiments.

Figure 3:
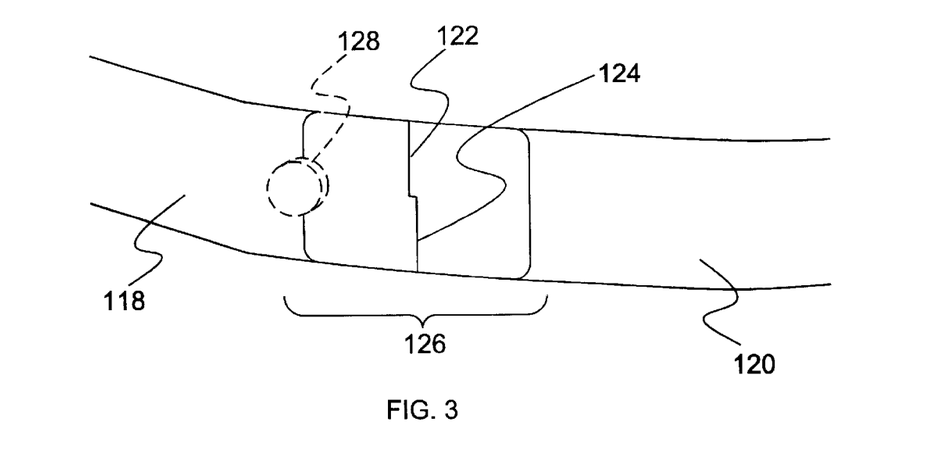
FIG. 3 is an enlarged view of only the flap-in-slot fastener area of the belt of FIG. 1, with its reinforced attachment from an accessory magnet that is optionally affixed magnetically over one end of the overlapping, interlocking straps.

FIG. 3 shows an accessory magnet 128 reinforcing the flap-in-slot fastener 126 in which overlapping left strap 118 and right strap 120 are joined through interlaid left slit 122 and right slit 124, thereby firmly fastening the belt of FIG. 1. Accessory magnet 128 can optionally be placed magnetically over both interlocking, overlapping straps at the outermost strap's edge where a short, second layer is formed over the inner strap. Accessory magnet 128 is identical to each powerful magnet 110, so it is strong enough to help bind together the two straps. Through its strong attraction to the straps' magnetizable metal, accessory magnet 128 prevents any tiny tilting of the flap-ike strap ends.

Flap-in-slot fastener 126 may be substituted by another fastener subsequently described in other belt embodiments.

Figure 4:
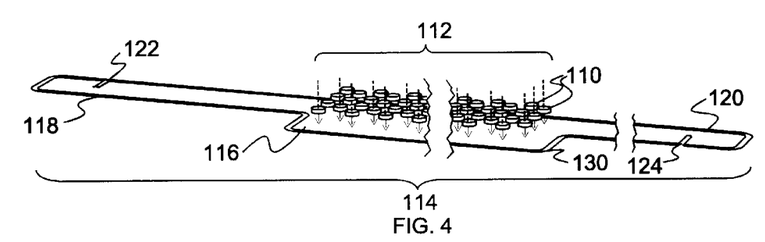
FIG. 4 is an isometric exploded view of the belt of FIG. 1, which indicates how the magnets are placed into a strategic array onto the supporting portion's larger center.

FIG. 4 shows how several duplicates of magnet 110 are arranged into the magnet array 112 and placed onto the larger center 116 of the belt of FIG. 1. These magnets adhere directly to magnetizable supporting portion 114 through strong magnetic attraction. Supporting portion 114 firmly maintains each magnet 110 in a separate spot across its stable, sturdy surface. So, since supporting portion 114 keeps magnet array 112 stabilized, the belt does not magnetically collapse in on itself. In contrast, collapse occurs in a non-magnetizable material supporting portion that is not sturdy enough to stop strong magnets from attracting forcefully across its flimsy surface.

Each magnet 110 is essentially identical, as the same materials and processes are used to mass produce these magnets. These static-field permanent magnets can be purchased from a supplier, which can be found through the Thomas Register.

Each magnet 110 is sufficiently strong to disintegrate fat. More specifically, these are neodymium-based, samarium-based, or other comparably strong magnets of at least around 4,000 gauss, and preferably more. In contrast, other bio-magnets in commercially-available back-support belts are typically less than 4,000 gauss in manufacturer's strength rating.

Each magnet 110 is preferably between about 0.18 and 0.25 inches in thickness, because strong magnets in this dimension range are thin enough to keep the belt concealable, and are thick enough to provide appropriate field penetration into body fat. Because the belt's magnet material is so strong, it inherently offers enough penetrative powers without help from any other sources. The belt's magnets may be thinner or thicker than this recommended range of dimensions.

Each magnet 110 has a north and south pole, which corresponds with a negative and positive magnetic field, respectively. These magnets are preferably magnetized "conventionally" so negative and positive fields are separated on opposite faces. More specifically, like a coin with a heads side and a tails side, each magnet would have a positive field face and a negative field face. With this magnetic design, the belt wearer's torso could be exposed maximally to negative magnetic fields while only minimally to positive magnetic fields. However, these magnets could have alternative magnetization arrangements, as there are various ways to design magnets so as to expose the body to different concentrations of negative and positive fields.

Each magnet 110 is preferably between about 0.5 and 1.0 inches in diameter, because magnets in this range are expansive enough to contribute sufficiently to the belt's overall magnetic surface area, and are narrow enough to avoid detracting from the belt's flexibility and field strength as related to these magnets' preferred thicknesses. However, the diameter of each magnet 110 may be greater or lesser than this recommended range.

Each magnet 110 is a disc because this circular shape fits optimally into the alternating pattern of magnet array 112 that densely distributes magnetic fields. However, the belt's magnets could have other shapes, such as squares or rectangles.

Each magnet 110 may be substituted by another magnet subsequently described in other belt embodiments. Magnet array 112 may be substituted by another magnet array subsequently described in other belt embodiments.

Magnet array 112 is established on larger center 116 by placement of magnets in staggered positions between alternating odd- and even-numbered columns. Each column may be formed progressively through placement of each magnet 110 individually in line from top to bottom, or otherwise. Around these magnets are small spaces that allow for flexibility of the supporting portion's larger center.

In the magnet array of FIG.4, the first column, which is an example of an odd-numbered one, includes four magnets. Furthermore, only three spaces occur vertically between these magnets. However, these specific numbers of magnets and spaces are for illustrative purposes only, and will generally vary according to the overall appropriate size of the magnet array. The first magnet is placed right at the top edge of the supporting portion's larger center. Also, at the bottom edge of the supporting portion's larger center, the fourth and last magnet is placed. However, these specific placements of magnets may vary.

In contrast, only three magnets occupy the second, or even-numbered, adjacent column in the magnet array of FIG. 4. Furthermore, four spaces occur vertically within this column. However, these specific numbers of magnets and spaces are for illustrative purposes only, and will generally vary according to the overall appropriate size of the magnet array. The first magnet is placed below the space at the top edge of the supporting portion's larger center. The third and last magnet is placed above the space at the bottom edge of the supporting portion's larger center. However, these specific placements of magnets may vary.

It is preferable to have the south poles or positive magnetic fields of all magnets placed face down on the larger center's inner surface. It is also preferable to have the north poles or negative magnetic fields of all magnets facing up and away from the larger center's inner surface. In this way, the belt wearer's torso is exposed mostly to negative magnetic fields. However, it is possible to arrange magnetic polarities otherwise.

Figure 5:
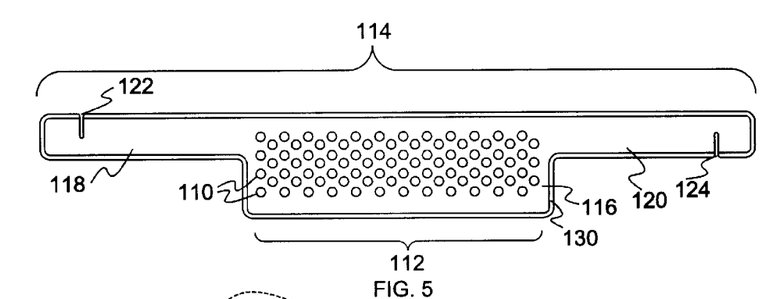
FIG. 5 shows the entire magnet array attached to the larger center of the supporting portion of the belt of FIG. 1.

FIG. 5 shows magnet array 112 completely set in place on the larger center 116 of supporting portion 114. The placement and amount of magnets and spaces differs between odd- and even-numbered columns in the magnet array. For example, as illustrated, all odd-numbered columns may include four magnets and three spaces, whereas all even-numbered columns may conversely include three magnets and four spaces.

This staggered placement of magnets and spaces creates an alternating pattern across the supporting portion's larger center. More specifically, magnets in any column align horizontally with adjoining columns' spaces, not their magnets. So, like a checkerboard's red squares, adjacent magnets come closest on a diagonal. These diagonal angles allow for more density of magnetic field distribution while preserving the flexibility of the supporting portion's larger center.

Furthermore, spaces in any column align horizontally with adjacent columns' magnets, not their spaces. So, like a checkerboard's black squares, adjacent spaces come closest on a diagonal.

Spaces between magnets in the magnet array 112 range from about 0.25 to 0.375 inches across, but could be narrower or wider than these dimensions. Generally, spaces should be as narrow as permissible by belt flexibility needs or magnetic flux forces.

The magnet array of FIG. 5 includes 84 magnets in 24 columns maintained on the supporting portion's larger center. However, this specific number of and distribution of magnets will generally vary according to the size of the belt, particularly one whose larger center is broader or narrower, or higher or lower. More specifically, the higher the supporting portion's larger center, the more magnets per column. So, for example, a 6" high belt could include about five magnets 110 per column. Also, the broader the supporting portion's larger center, the more columns of magnets. So, for example, a larger center that is 30" broad could include about 30 columns of magnets 110.

A broader, higher belt for a person with a bigger torso would thus include more magnets in total than illustrated. For example, a belt with a 6"×30" larger center would probably include 135 magnets 110, not just 84 as shown. Even with a greater number of magnets, a larger belt will preferably still maintain the alternating pattern of the magnet array. This alternating spatial scheme would simply extend with the additional magnets and columns.

Figure 6:
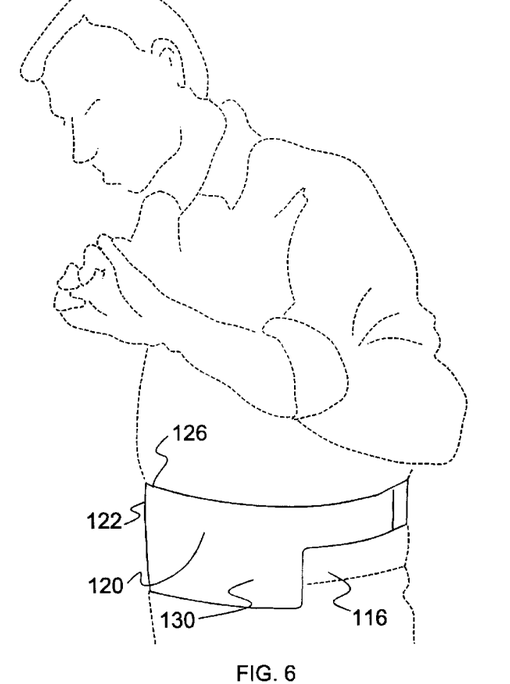
FIG. 6 shows the use and appearance of the belt of FIG. 1 as worn around a human torso.

The operation of the above-described embodiment of the invention is illustrated with respect to FIG. 6.

FIG. 6 shows the belt of FIG. 1 from the outer side, as it would appear when worn around one's torso. Although this drawing figure shows how the belt's magnetic larger center can be positioned over the wearer's belly area, other torso areas can be targeted with these magnets by moving the larger center so it covers the desired area. Thus, for instance, to counteract fat within the buttocks, the belt's magnetic larger center would be positioned over the buttocks, so the belt would be fastened around the belly area. The belt could be fastened around the torso so its magnets target the belly, buttocks, back, lateral or upper abdomen. The belt should be large enough to wrap around the wearer's torso and cover his or her desired target area.

Figure 7:
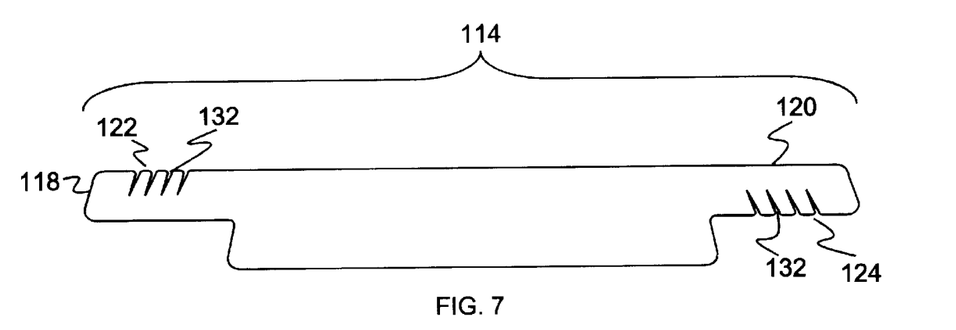
FIG. 7 shows the extra slits on the straps of the belt of FIG. 1.

FIG. 7 shows how the supporting portion of the belt of FIG. 1 can have one or more extra slits cut into its strap section to enable an adjustable, flap-in-slot fastener according to the wearer's changing torso circumference. More specifically, each extra slit 132 is deep enough in the strap section of supporting portion 114 to enable secure attachment of the belt, but shallow enough so each flap is sufficiently sturdy for fastening.

Figure 8:
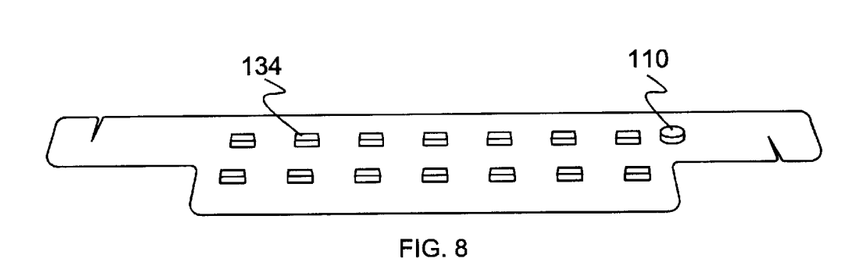
FIG. 8 shows the alternative magnets that differ from the magnets of FIG. 1, yet can be used in the belt.

Many other modifications of the therapeutic magnet belt, some of which are described herein, are possible. For instance:

FIG. 8 shows how another embodiment of the belt can comprise magnets of characteristics that differ from those of magnet 110. More specifically, as indicated with alternative magnet 134, other belt magnets can differ in size, being either smaller or larger in any dimension, such as thickness. Furthermore, as alternative magnet 134 also shows, instead of a circular diameter, other belt magnets can have rectangular length and width, or other shapes. Other belt magnets can differ in color, especially if they are coated or contain various elements. Neodymium, samarium, nickel, cobalt, iron, or other strongly-magnetic elements can be included in other belt magnets. So, other magnets can vary in strength, being either stronger or weaker, between different or even within the same belt. Other belt magnets can differ in more miscellaneous characteristics, such as degree of rigidity, or even type, as in magnets other than static-field permanent ones. Other magnets can be designed with polarity patterns that differ from the one described as preferred. The number of magnets in the belt can easily vary, as shown in FIG. 8 and FIG. 9.

Figure 9:
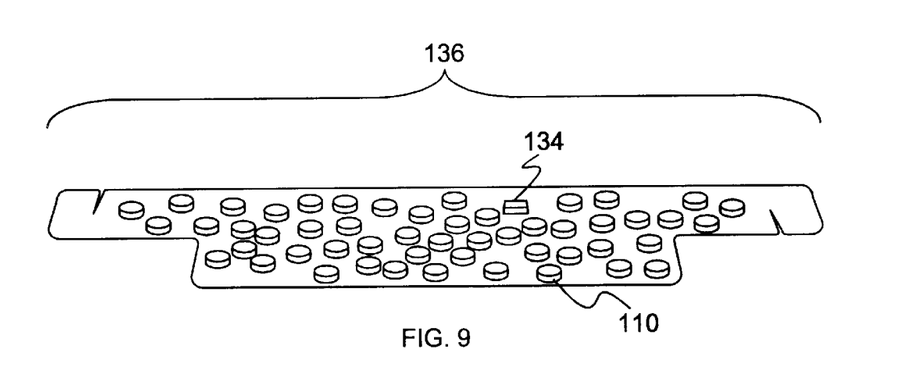
FIG. 9 shows the alternative magnet array that differs from the magnet array of FIG. 1, yet can be used in the belt.

FIG. 9 shows how another embodiment of the belt can have a plurality of magnets arranged in a pattern other than the staggered alternation of magnet array 112. More specifically, as indicated with alternative magnet array 136, magnets can be placed in more random positions across the belt's entire supporting portion, including the strap section of the supporting portion. Other belt magnets can be arranged in a grid-like formation, as indicated in FIG. 8, or in another alternating pattern with slightly different spacing. As alternative magnet array 136 also indicates, other belts can easily offer somewhat greater or lesser overall surface area of magnets, and thus target somewhat more or less of the wearer's torso, provided the coverage area is substantial enough for effects.

Figure 10:
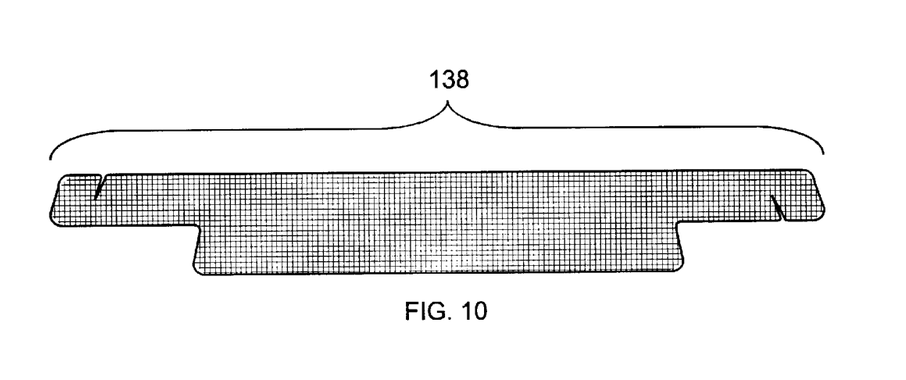
FIG. 10 shows the reticulated weave supporting portion that differs from the supporting portion of FIG. 1, yet can replace it in the belt.

FIG. 10 shows that another embodiment of the belt can comprise a reticulated weave supporting portion 138. While the non-solid surface of the reticulated weave enables ventilation and lightens the belt's weight, it offers less contact area for support. So, the reticulated weave supporting portion 138 is preferably a magnetizable metal mesh that strongly attracts the magnets.

Figure 11:
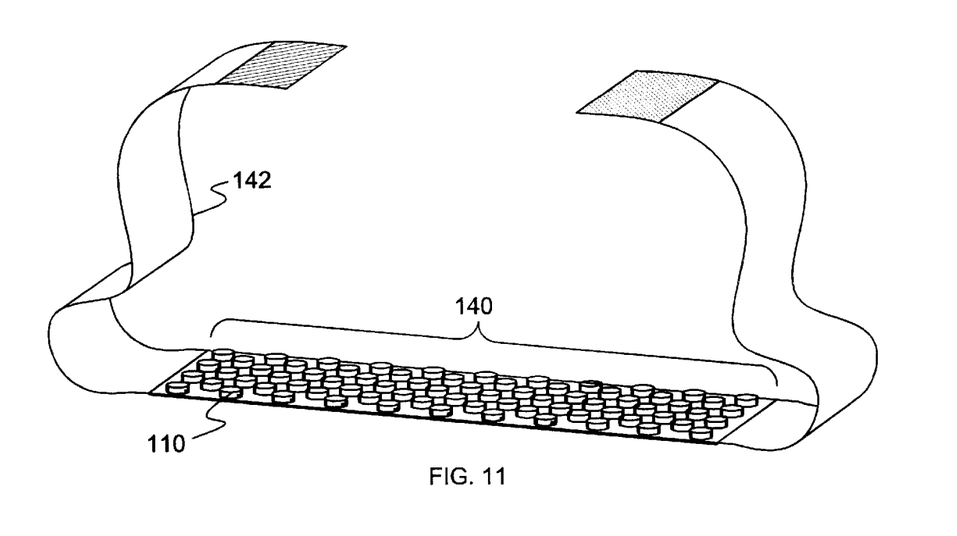
FIG. 11 shows the combination of magnetizable and non-magnetizable materials that combine to comprise a supporting portion for the belt.

FIG. 11 shows that another embodiment of the belt can comprise both magnetizable and non-magnetizable material, which structurally combine for function. More specifically, a non-circuitous supporting portion 140 is similar to the larger center 116 of supporting portion 114 in that it magnetically maintains the magnet array on its inner surface. However, since the non-circuitous supporting portion does not wrap completely around the wearer's whole torso, it is joined with a non-magnetizable material 142 that acts as a straplike fastener for the belt. More specifically, the non-magnetizable material is preferably a rectangular fabric strap that loops around the whole torso and attaches to its own overlapping ends through a hook-and-loop or other fastener. By being magnetically sandwiched between the magnets and the magnetizable non-circuitous supporting portion, the self-fastening non-magnetizable material strap suspends the entire belt-like magnetic apparatus around the wearer's torso. Or, the non-magnetizable material 142 can comprise two or more non-circuitous straps that combine to wrap around the torso and join with complementary fasteners, thereby securing the belt on the wearer. These non-circuitous straps can be attached to the non-circuitous supporting portion by way of heavy-duty staples, adhesive substances, or other strong bonding means. The non-magnetizable material can include cotton, polyester, polypropylene, neoprene, or other non-magnetizable fibers.

Figure 12:
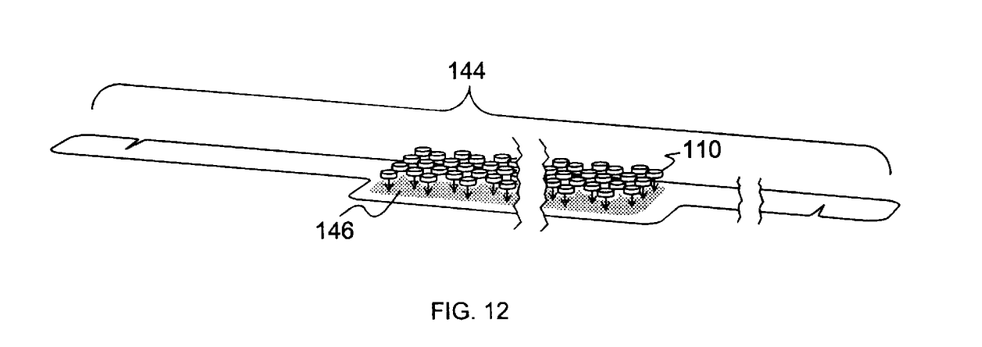
FIG. 12 shows the non-magnetizable supporting portion that calls for an additional attachment means for the magnets.

FIG. 12 shows that another embodiment of the belt can comprise a non-magnetizable supporting portion 144 that is flexible enough to conform to the contours of the wearer's torso, yet is also sturdy enough to withstand creasing from the attractive strength among the magnets it supports. The non-magnetizable supporting portion can comprise plastic, aluminum, copper, chromium, cardboard, or other functional non-magnetizable material. Thanks to the sturdiness of its material, the non-magnetizable supporting portion should be able to serve also as a fastener itself, as in another flap-in-slot fastener. Otherwise, one or more separate straplike fasteners, which could comprise sturdy magnetizable metal, would be attached to the non-magnetizable supporting portion. Furthermore, an additional attachment means 146 would be needed to join the magnets with the non-magnetizable supporting portion. The additional attachment means 146 can comprise an adhesive substance, such as glue, or other sticky material, such as tape.

Figure 13:
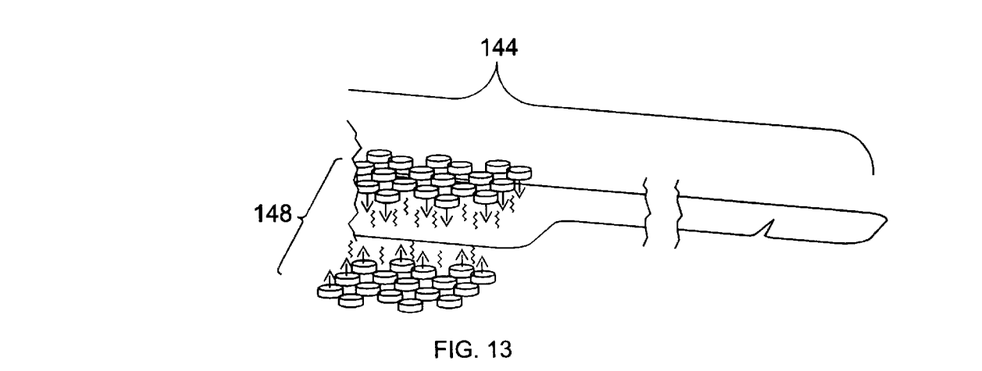
FIG. 13 shows how magnetic attraction serves as the additional attachment means to join the magnets with the non-magnetizable supporting portion of FIG. 12.

Or, as shown in FIG. 13, an additional magnetic attachment means 148 can be used to unite the magnets and non-magnetizable supporting portion 144 through magnetic attraction. More specifically, additional magnets can be placed strategically on the outer surface so they attract through the non-magnetizable supporting portion to the inner-surface magnets, thereby collectively suspending themselves.

Figure 14:
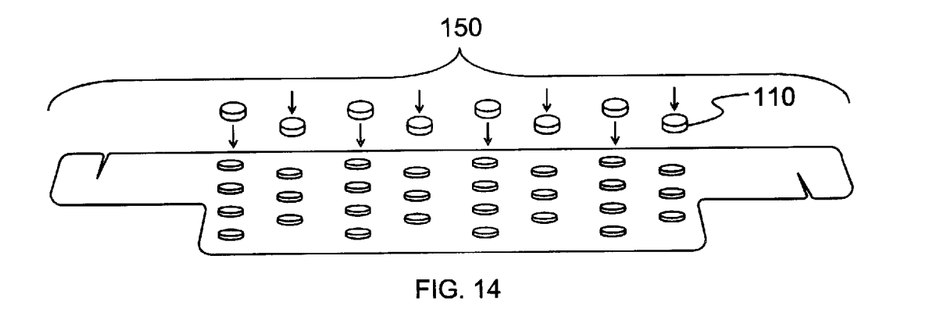
FIG. 14 shows the perforated supporting portion that differs from the supporting portion of FIG. 1, yet can replace it in the belt.

FIG. 14 shows that another embodiment of the belt can comprise a perforated supporting portion 150 including a plurality of through openings. The through openings can serve to embed the magnets on the same plane, which can block forceful attraction between magnets and thereby prevent collapse of a less sturdy, non-magnetizable material belt. Or, the through openings can serve to ventilate the belt. The perforated supporting portion could comprise magnetizable material, such as a flexible magnet strip, or non-magnetizable material, such as plastic or other sturdy fibrous or polymeric substances.

Figure 15:
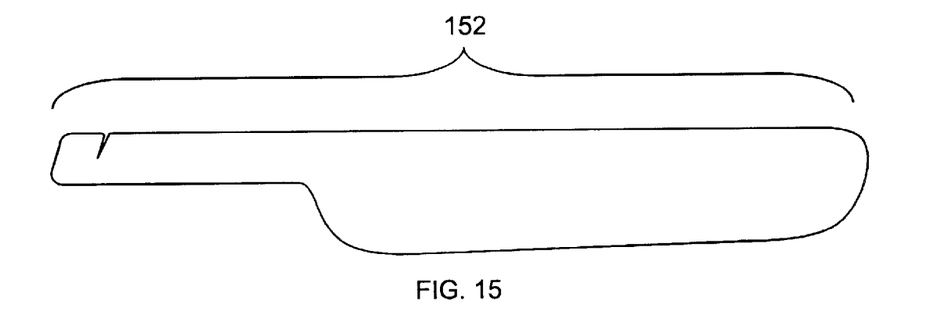
FIG. 15 shows the single-strap supporting portion that differs from the supporting portion of FIG. 1, yet can replace it in the belt.

FIG. 15 shows how another embodiment of the belt can have only one strap, instead of two or more, through a single-strap supporting portion 152. The single-strap supporting portion 152 can be wrapped around the wearer's whole torso so the end of its strap section circuitously connects with its larger section. At this overlapping area or connection point, the single-strap supporting portion 152 can be fastened magnetically or otherwise, thereby securing the entire belt on the wearer. The single-strap supporting portion also shows how the belt can be shaped differently. More specifically, the supporting portions of other belts can be larger or smaller in any dimension, including thickness, or be more or less contour-cut.

Figure 16:
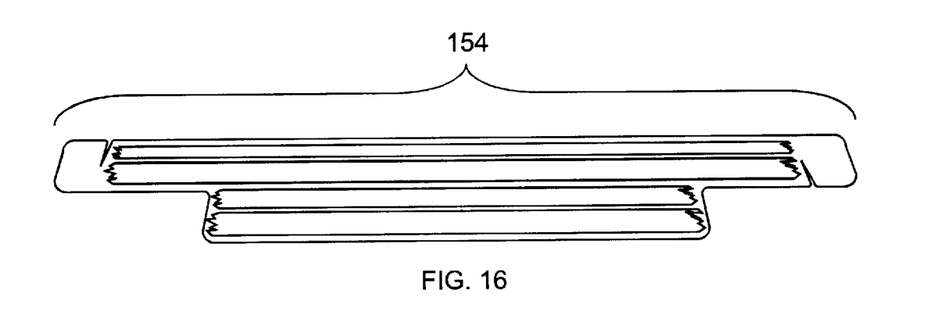
FIG. 16 shows the sheath that can cover the belt.

FIG. 16 shows how another embodiment of the belt can be covered with a sheath 154. The sheath preferably comprises hypo-allergenic cloth tape that can wrap around and adhere to the supporting portion and magnets on it. However, the sheath can comprise other material, such as non-adhesive cotton cloth, polyester, nylon, or other synthetic or natural fibers. The sheath can improve the belt's comfort, cleanliness, and camouflage. The sheath could also help contain the magnets on the supporting portion. So, although optional, other elements or components, such as the sheath, can be added to the belt. For example, sheath 154 can be wrapped over magnet array 112 on supporting portion 114.

Figure 17:
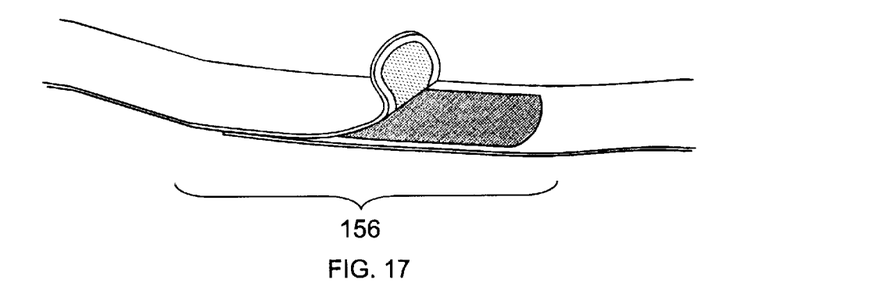
FIG. 17 is an enlarged view of a hook-and-loop fastener for the belt.

FIG. 17 shows how another belt embodiment can include a hook-and-loop fastener 156, instead of the flap-in-slot fastener 126 of the belt of FIG. 1. Hook-and-loop fastener 156 could even be adhesively added to the left and right straps of supporting portion 114. However, another belt embodiment would include hook-and-loop fastener 156 to serve as its means of attaching the ends of the belt around the wearer's torso.

Figure 18:
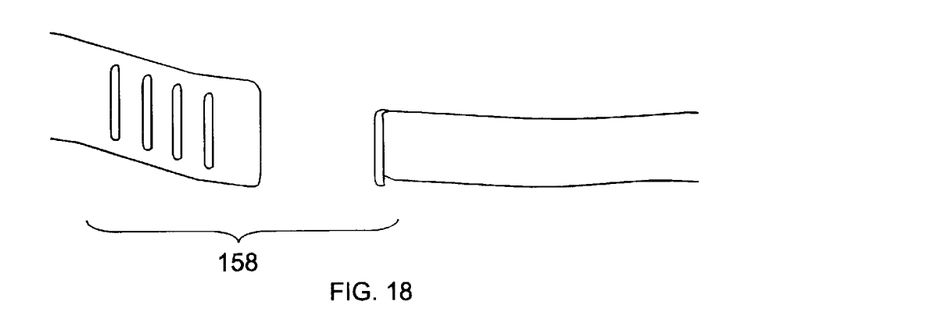
FIG. 18 is an enlarged view of a large hook-in-a-loop fastener for the belt.

FIG. 18 shows that another belt embodiment can include a large hook-in-a-loop fastener 158, which comprises just one sturdy hook that interlocks in an adjustable manner with any one of several large loops on the belt's strap section.

Figure 19:
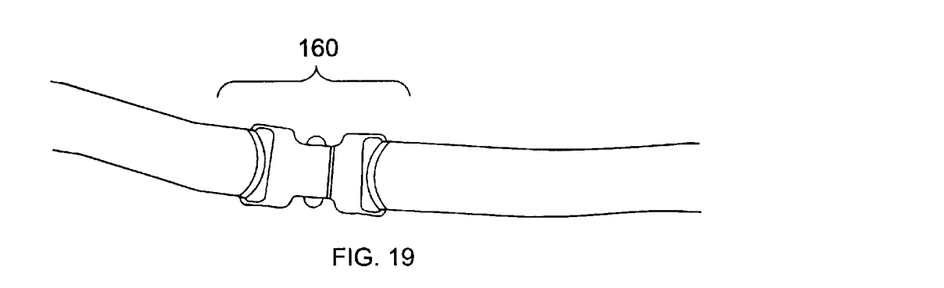
FIG. 19 is an enlarged view of a hook-in-loop-clasp fastener for the belt.

FIG. 19 shows that another belt embodiment can include a hook-in-loop-clasp fastener 160, which comprises just one adjustable clasp of the hook-and-loop type.

Figure 20:
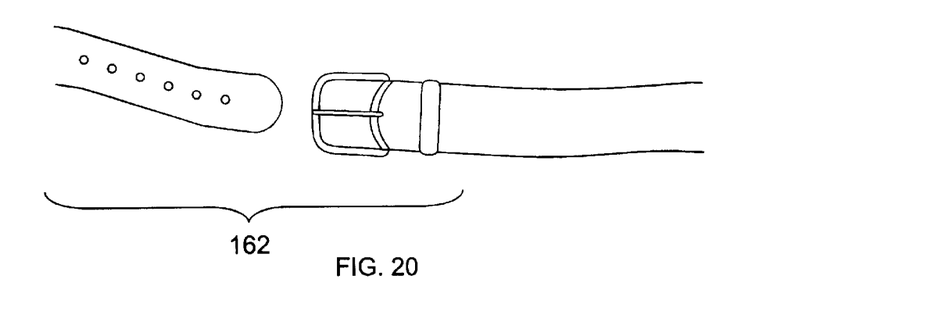
FIG. 20 is an enlarged view of a buckle fastener for the belt.

FIG. 20 shows how another belt embodiment can include a buckle fastener 162 to attach the belt.

Figure 21:
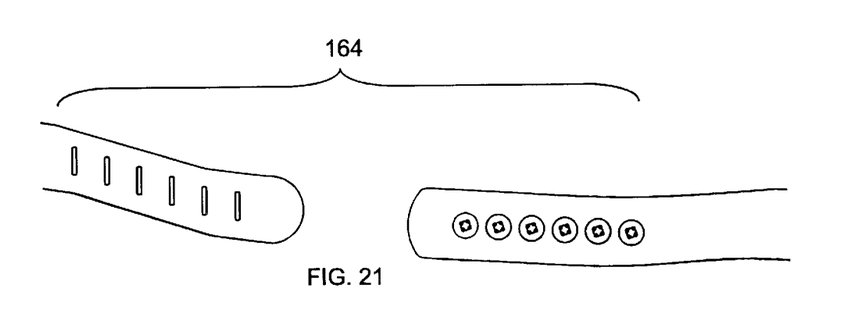
FIG. 21 is an enlarged view of a button fastener for the belt.

FIG. 21 shows that another belt embodiment can include a button fastener 164 to attach the belt.

Figure 22:
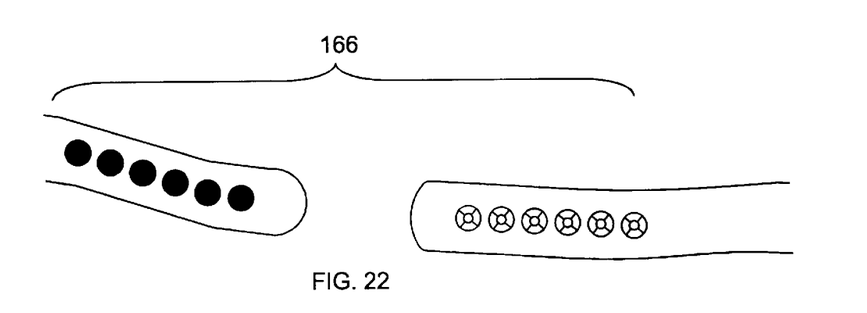
FIG. 22 is an enlarged view of a snap fastener for the belt.

FIG. 22 shows that another belt embodiment can include a snap fastener 166 to attach the belt.

Figure 23:
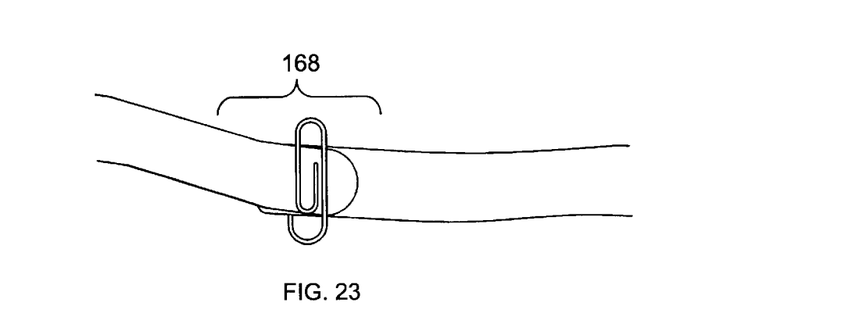
FIG. 23 is an enlarged view of a clip fastener for the belt.

FIG. 23 shows that another belt embodiment can include a clip fastener 168 to attach the belt.

Figure 24:
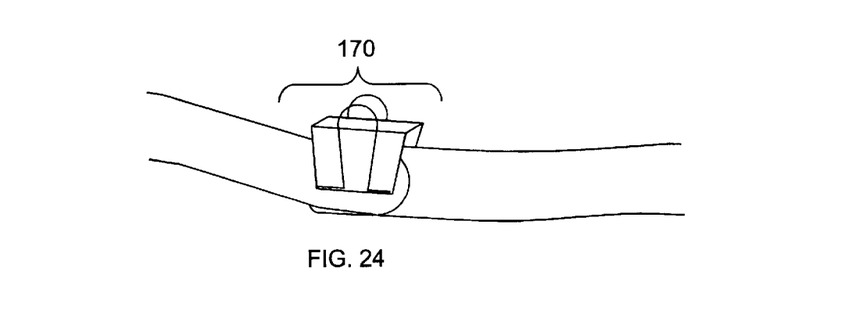
FIG. 24 is an enlarged view of a clamp fastener for the belt.

FIG. 24 shows that another belt embodiment can include a clamp fastener 170 to attach the belt.

Figure 25:
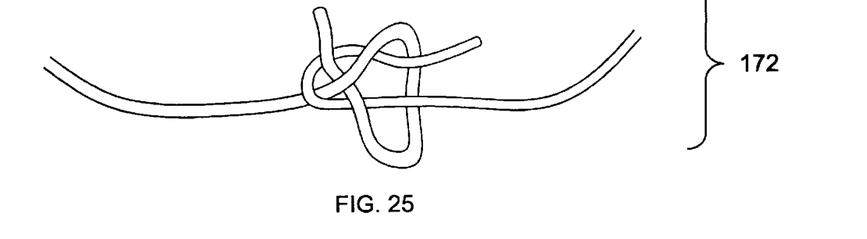
FIG. 25 is an enlarged view of a plurality of ties fastener for the belt.

FIG. 25 shows that another belt embodiment can include a plurality of ties fastener 172, which can also serve as straps.

Figure 26:
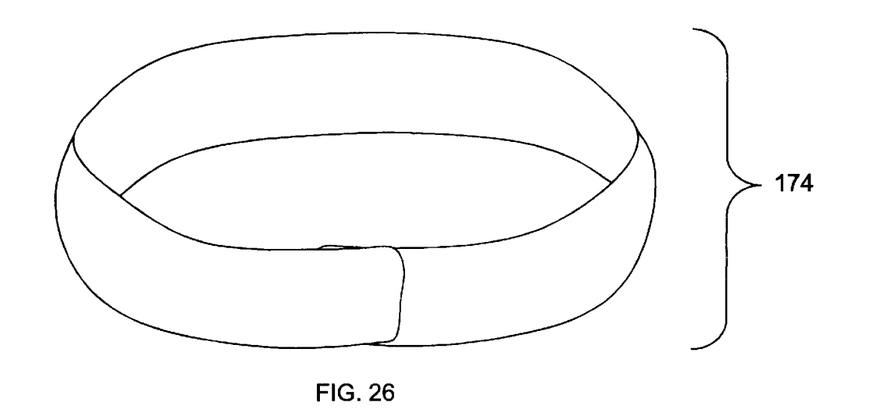
FIG. 26 shows the flexible magnetic strip that could solely serve as a therapeutic belt.

FIG. 26 shows an embodiment of a belt that could comprise only a flexible magnetic strip 174. More specifically, an idealistic future belt would be a magnetically self-fastened, sufficiently-large, flexible magnet strip of over 4,000 gauss strength. Packing neodymium or other comparably strong magnetic elements, this strip alone would literally cover the fat-decreasing functions of the belt of FIG. 1. It would look and feel somewhat like a proportionally-reduced piece of thicker conveyor belt at a supermarket checkout. Preferably, its wearer would place the magnetic strip's negative field face against the skin and then wrap it around the torso, where it would then be secured by simply overlapping it onto its opposing side's positive field face.

Figure 27:
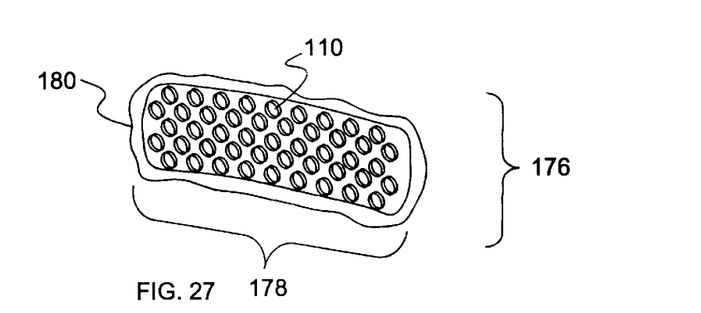
FIG. 27 shows an adhesive magnetic apparatus that could act as an applicator for the magnets.

FIG. 27 shows an embodiment of an adhesive magnetic apparatus 176 that invades the utility of this invention without involving a belt-like magnetic applicator. More specifically, at least one adequate magnet is attached to a non-circuitous strap-less supporting portion 178 that magnetically or otherwise maintains each magnet in position. Moreover, the assembly of magnet-and-non-circuitous strap-less supporting portion is collectively attached to an adhesive layer 180 that can be applied over a substantial area of the wearer's torso, such as the belly. The adhesive layer 180 is preferably a sufficiently-large strip of hypo-allergenic tape that necessarily has sufficiently-strong adhesive properties to enable the wearing of this entire apparatus for enough time to decrease fat.

Figure 28:
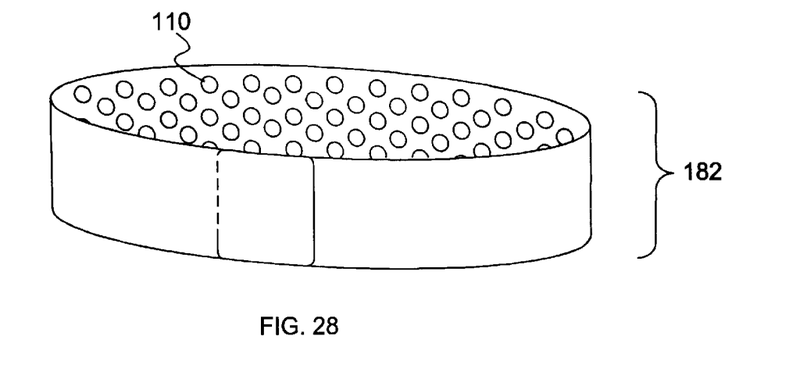
FIG. 28 shows a non-contour supporting portion that magnetically maintains and applies magnets.

FIG. 28 shows how another embodiment of the belt can comprise a non-contour supporting portion 182 that magnetically maintains the plurality of magnets on its entire inner surface, which also enables magnetic fastening of the whole apparatus.

The belt can be assembled from a kit that comprises a magnetizable supporting portion, such as supporting portion 114 of the belt of FIG. 3, and a plurality of magnets of about 4,000 to 40,000 gauss in strength, such as magnet array 112 of the belt of FIG. 3. The supporting portion in the kit is sufficiently flexible to conform to the contours of the wearer's torso and sufficiently rigid to prevent itself from creasing responsive to the magnets' strong fields. The kit can further include an optional sheath, such as hypo-allergenic cloth tape, to cover the magnets and supporting portion.

The therapeutic magnet belt constitutes a new method of decreasing fat content in a selected portion of a human body by a desired amount, in that it exposes the selected portion of the body to a magnetic field of sufficient strength, and maintains that magnetic field in the selected portion of the body until the fat content has been decreased by the desired amount.

The aforementioned plausible embodiments of the therapeutic magnet belt are among the most predictable. Through imitators' attempts to disguise their belts from mine, other elements could be used to substitute my magnets and supporting portion, or any number of elements could be added to the belt.

To assemble the belt of FIG. 1, appropriate parts are acquired, such as flexible magnetizable metal. Then, body measurements are taken, e.g., with a tape measure, to help find the right fit for the belt's application. For instance, the belt wearer's widest waist circumference, ventral distance between the torso's two widest sides, and height of target fat are preferably measured. Next, corresponding calculations are made to determine the belt's dimensions, such as the breadth of each strap, and then these are marked out onto the metal sheet serving as the supporting portion. Then, the belt's supporting portion is cut out from this larger, marked sheet. Next, each outer-pointing corner of this supporting portion is trimmed to a rounded edge, and slits are cut in the straps. Finally, magnets are affixed magnetically onto the larger center of the supporting portion in a staggered arrangement so spaces alternate with these magnets in a dense, expansive array across the belt's inner surface.

To use the belt of FIG. 1, one simply straps it on snugly around the torso, then lets it go. More specifically, first one uses one's hands to lift the belt by its straps and hold it close to the torso so the magnetic inner surface is upright and facing in toward the body. Then, holding these straps with one's hands out wide, the magnetic surface is pulled in against the torso and positioned precisely so the magnets cover the desired target areas, such as the belly, buttocks, lateral or upper abdomen. Next, this flexible yet sturdy belt is wrapped around the whole torso so the two straps eventually overlap. Once the belt is bent inward enough so it tightly hugs the body, it is fastened at this fitting spot by interlocking the flap and slit of the overlapping straps. Since the belt wearer's torso may shrink over time, the point of flap-in-slot fastening can be modified for the best, snug fit at any time by simply cutting new slits as and where needed. The wearer can also stick an optional accessory magnet over the outermost edge of the interlocking, overlapping straps to reinforce the belt's attachment.

It will be apparent to those skilled in the art that the assembly and operation methods for the belt involve some degree of variability, differing particularly according to the chosen embodiment.

By simply wearing the belt over a sufficient period of time, and thereby targeting a torso area with such a strong magnetic field, the fat exposed to the magnetic field gradually dissolves. This happens because the majority of nuclei of hydrogen atoms abundant in fat align themselves with the external magnetic field, which de-stabilizes and ultimately breaks down the electron-sharing bonds between fat's hydrogen and carbon atoms.

So, the therapeutic magnet belt is an efficient fat-loss product whose external and extendible application is atypical among "weight loss" methods, and whose structure and function are unique to all other magnetic belts, which are designed simply for potential lower back pain relief.

The belt can also relieve back pain, just like other magnetic belts, by wearing it so its larger magnetic section covers the wearer's lower back. The belt can be worn around a wearer's torso in various ways so, for example, its larger magnetic section covers his or her belly or buttocks.

Although the foregoing description includes many specificities, these should not be construed as limitations on this invention's scope. Rather, they constitute exemplifications of preferable embodiments among many possible variations of the belt. Ultimately, the appended claims and their equivalents, not the illustrated embodiments, should determine this invention's scope.

The invention claimed is:

1. A therapeutic belt for placement around a wearer's torso for activating a fat reduction procedure in fat cells adjacent to the placement of said therapeutic belt, the belt comprising:
    a supporting portion, and
    a plurality of magnets attached to said supporting portion, each of said plurality of magnets having a magnetic-field strength from about 4,000 to about 40,000 gauss, and said plurality of magnets having a combined magnetic flux density of at least 100,000 gauss,
    said plurality of magnets being placed with respect to each other and with respect to said supporting portion so as to concentrate the magnetic field strength of said magnets toward said fat cells adjacent to the placement of said therapeutic belt.

2. The therapeutic belt of claim 1 wherein said supporting portion is sufficiently flexible to conform to the contours of the wearer's torso and sufficiently rigid to prevent said supporting portion from creasing responsive to the magnetic fields of said plurality of magnets.

3. The therapeutic belt of claim 2 wherein said supporting portion is magnetizable, said plurality of magnets being magnetically attached to said supporting portion.

4. The therapeutic belt of claim 3 further including a sheath, said supporting portion and said plurality of magnets covered by said sheath.

5. The therapeutic belt of claim 4 wherein said sheath possesses hypo-allergenic properties.

6. The therapeutic belt of claim 3 wherein said supporting portion includes a plurality of through openings.

7. The therapeutic belt of claim 3 wherein said supporting portion comprises a reticulated weave.

8. The therapeutic belt of claim 3 wherein said supporting portion further includes a fastener.

9. The therapeutic belt of claim 3 further including at least one strap extending from said supporting portion.

10. The therapeutic belt of claim 9 wherein said at least one strap is magnetizable.

11. The therapeutic belt of claim 10 wherein said at least one strap further includes a fastener.

12. The therapeutic belt of claim 9 wherein said at least one strap is non-magnetizable and includes a fastener.

13. The therapeutic belt of claim 3 further including a plurality of ties extending from said supporting portion.

14. The therapeutic belt of claim 2 wherein said supporting portion is non-magnetizable.

15. The therapeutic belt of claim 14 wherein said supporting portion includes a plurality of openings corresponding to said plurality of magnets, each of said plurality of magnets positioned in one of said plurality of openings.

16. The therapeutic belt of claim 14 further including a sheath, said supporting portion and said plurality of magnets covered by said sheath.

17. The therapeutic belt of claim 16 wherein said sheath possesses hypo-allergenic properties.

18. The therapeutic belt of claim 14 further including at least one strap extending from said supporting portion, said at least one strap having a fastener.

19. The therapeutic belt of claim 14 further including a plurality of ties extending from said supporting portion.

20. A kit for constructing a therapeutic belt for placement around a wearer's torso for activating a fat reduction procedure in fat cells adjacent to the placement of said therapeutic belt, the kit comprising:

a magnetizable supporting portion, and a plurality of magnets which magnetically adhere to said magnetizable supporting portion when placed thereon, each of said plurality of magnets having a magnetic-field strength from about 4,000 to about 40,000 gauss, and said plurality of magnets having a combined magnetic flux density of at least 100,000 gauss, said plurality of magnets being placed with respect to each other and with respect to said magnetizable supporting portion so as to concentrate the magnetic field strength of said magnets toward said fat cells adjacent to the placement of said therapeutic belt.

21. The kit of claim 20 wherein said magnetizable supporting portion is sufficiently flexible to conform to the contours of the wearer's torso and sufficiently rigid to prevent said magnetizable supporting portion from creasing responsive to the magnetic field of said plurality of magnets.

22. The kit of claim 21 further including a sheath for covering said magnetizable supporting portion and said plurality of magnets.

23. The kit of claim 22 wherein said sheath possesses hypo-allergenic properties.

24. The kit of claim 21 wherein said magnetizable supporting portion includes a plurality of through openings.

25. The kit of claim 21 wherein said magnetizable supporting portion comprises a reticulated weave.

26. The kit of claim 21 wherein said magnetizable supporting portion further includes a fastener.

27. The kit of claim 21 wherein said magnetizable supporting portion further includes at least one strap.

28. The kit of claim 27 wherein said at least one strap further includes a fastener.

29. The kit of claim 21 further including at least one non-magnetizable strap for attaching said magnetizable supporting portion to the wearer's torso, said non-magnetizable strap having a fastener.

30. The kit of claim 21 further including a plurality of ties for attaching said magnetizable supporting portion to the wearer's torso.

31. A method of decreasing fat content in a selected portion of a human body by a desired amount, said method comprising:

placing a therapeutic belt around said selected portion of a human body, said belt having a supporting portion and a plurality of magnets attached to said supporting portion, each of said plurality of magnets having a magnetic-field strength from about 4,000 to about 40,000 gauss, and said plurality of magnets having a combined magnetic flux density of at least 100,000 gauss, arranging said magnets with respect to each other and with respect to said supporting portion so as to concentrate the magnetic field strength of said magnets toward fat cells adjacent to the placement of said therapeutic belt at said selected portion of the human body, exposing the selected portion of the human body to a magnetic field of sufficient strength from said magnets attached to said supporting portion; and maintaining said magnetic field in the selected portion of the human body until the fat content in said selected portion has decreased by the desired amount.

* * * * *